(12) United States Patent
Lun

(10) Patent No.: US 9,594,869 B2
(45) Date of Patent: Mar. 14, 2017

(54) GENETICALLY ENGINEERED MICROBES AND USES THEREOF

(75) Inventor: Desmond Siu Men Lun, Philadelphia, PA (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 662 days.

(21) Appl. No.: 14/001,299

(22) PCT Filed: Mar. 1, 2012

(86) PCT No.: PCT/US2012/027219
§ 371 (c)(1),
(2), (4) Date: Oct. 18, 2013

(87) PCT Pub. No.: WO2012/118933
PCT Pub. Date: Sep. 7, 2012

(65) Prior Publication Data
US 2014/0039232 A1    Feb. 6, 2014

Related U.S. Application Data

(60) Provisional application No. 61/447,746, filed on Mar. 1, 2011.

(51) Int. Cl.
| | | |
|---|---|---|
| *C12N 1/21* | (2006.01) |
| *C12P 7/64* | (2006.01) |
| *C12P 5/02* | (2006.01) |
| *G06F 19/12* | (2011.01) |
| *C12N 9/02* | (2006.01) |
| *C12N 9/10* | (2006.01) |
| *C12N 9/90* | (2006.01) |
| *C12N 1/20* | (2006.01) |
| *C10G 3/00* | (2006.01) |

(52) U.S. Cl.
CPC .............. *G06F 19/12* (2013.01); *C10G 3/50* (2013.01); *C12N 1/20* (2013.01); *C12N 9/001* (2013.01); *C12N 9/1022* (2013.01); *C12N 9/90* (2013.01); *C12P 7/6409* (2013.01); *C12Y 103/99003* (2013.01); *C12Y 202/01002* (2013.01); *C12Y 501/03001* (2013.01); *Y02P 20/52* (2015.11); *Y02P 30/20* (2015.11)

(58) Field of Classification Search
CPC .................................................... C12P 7/6409
See application file for complete search history.

(56) References Cited

U.S. PATENT DOCUMENTS

| | | |
|---|---|---|
| 2005/0124010 A1 | 6/2005 | Short et al. |
| 2008/0229654 A1 | 9/2008 | Bradin |
| 2008/0270096 A1 | 10/2008 | Palsson |
| 2009/0275097 A1 | 11/2009 | Sun et al. |

FOREIGN PATENT DOCUMENTS

| | | |
|---|---|---|
| WO | 2007027955 A2 | 3/2007 |

OTHER PUBLICATIONS

T. Baba et al. Construction of *Escherichia coli* K-12 in-frame, single-gene knockout mutants: the Keio collection, Molecular Systems Biology Article No. 2006:0008 (2006).*
T. Baba et al. Construction of *Escherichia coli* K-12 in-frame, single-gene knockout mutants: the Keio collection, Molecular Systems Biology Article No. 2006:0008 (2006). Supplementary Table 3.*
T. Baba et al. Construction of *Escherichia coli* K-12 in-frame, single-gene knockout mutants: the Keio collection, Molecular Systems Biology Article No. 2006:0008 (2006). descriptions of Supplementary materials available www.nature.com/msb.*
K. Nakahigashi et al."Systematic phenome analysis of *Escherichia coli* multiple-knockout mutants reveals hidden reactions in central carbon metabolism", Molecular Systems Biology 5:306 pp. 1-14 and Supplementary Materials (2009).*
Steen et al. "Microbial Production of Fatty-Acid Derived Fuels and Chemicals From Plant Biomass." Nature 463(7280): 559-562. (2010).

\* cited by examiner

*Primary Examiner* — Rebecca Prouty
(74) *Attorney, Agent, or Firm* — Fox Rothschild LLP

(57) ABSTRACT

This invention concerns methods of identifying genetic alterations with which a microbe can be used to produce fatty acids at a large amount for making biofuels. Also disclosed are microbes with such genetic alterations and uses thereof.

10 Claims, 7 Drawing Sheets

```
modelname  = iaf1260-ffa
nbhdsz     = 1
M          = 1
maxknock   = 10
bruteforce = 0

Loading model "iaf1260-ffa" ...

Loading "iaf1260-ffa.txt" ...
Compressing network ...
nmetab = 1745; nrxn = 2536; nbin = 913
Biomass flux:   0.802943
Synthetic flux:  [0.472506, 0.472506] of 5.098657
nmetab = 712; nrxn = 1356; nbin = 765
Biomass flux:   0.802943
Synthetic flux:  [0.472506, 0.472506] of 5.098657
nmetab = 646; nrxn = 1306; nbin = 726
Biomass flux:   0.802943
Synthetic flux:  [0.472506, 0.472506] of 5.098657
nmetab = 644; nrxn = 1304; nbin = 723
Biomass flux:   0.802943
Synthetic flux:  [0.472506, 0.472506] of 5.098657
nmetab = 644; nrxn = 1304; nbin = 723
Calculating vmin and vmax ...
Removing extraneous nodes and reactions ...
nmetab = 607; nrxn = 1185; nbin = 663
Compressing network ...
nmetab = 607; nrxn = 1185; nbin = 663
Biomass flux:   0.802943
Synthetic flux:  [0.472506, 0.472506] of 5.098657
nmetab = 586; nrxn = 1164; nbin = 663
Biomass flux:   0.802943
Synthetic flux:  [0.472506, 0.472506] of 5.098657
nmetab = 583; nrxn = 1164; nbin = 663
Biomass flux:   0.802943
Synthetic flux:  [0.472506, 0.472506] of 5.098657
nmetab = 583; nrxn = 1164; nbin = 663
Reduced network saved to 'iaf1260-ffa.reduced.mat'.
nmetab = 583; nrxn = 1164; nbin = 663
Biomass flux:   0.802943
Synthetic flux:  [0.472506, 0.472506] of 5.098657
Inflows:
     EX_ca2(e)                       -0.004
     EX_cl(e)                        -0.004
     EX_cobalt2(e)                   -0.003
     EX_cu2(e)                       -0.003
     EX_fe2(e)                       -0.006
     EX_fe3(e)                       -0.006
     EX_glc(e)                      -10.000
     EX_k(e)                         -0.143
     EX_mg2(e)                       -0.006
     EX_mn2(e)                       -0.003
     EX_mobd(e)                      -0.003
     EX_nh4(e)                       -8.659
     EX_o2(e)                       -17.751
     EX_pi(e)                        -0.772
     EX_so4(e)                       -0.201
     EX_zn2(e)                       -0.003
Outflows:
     EX_co2(e)                       21.646
     EX_h(e)                          7.375
     EX_h2o(e)                       43.423
     EX_myrsACP                       0.046
     EX_tdeACP                        0.114
     EX_palmACP                       0.034
     EX_hdeACP                        0.040
```

FIG. 1A

```
        EX_ddcaACP                      0.021
        EX_dcaACP                       0.028
        EX_ocACP                        0.190
        Biomass                         0.803

Performing 1-OPT local search ...

Iteration 1
-----------

Biomass flux:   0.787129
Synthetic flux: [0.569028, 0.569028] of 5.098657
Knockout cost:  1
Knockouts:
        ((b0221))
Inflows:
        EX_ca2(e)                      -0.004
        EX_cl(e)                       -0.004
        EX_cobalt2(e)                  -0.002
        EX_cu2(e)                      -0.002
        EX_fe2(e)                     -10.687
        EX_glc(e)                     -10.000
        EX_h(e)                        -3.451
        EX_k(e)                        -0.140
        EX_mg2(e)                      -0.006
        EX_mn2(e)                      -0.002
        EX_mobd(e)                     -0.002
        EX_nh4(e)                      -8.488
        EX_o2(e)                      -20.000
        EX_pi(e)                       -0.757
        EX_so4(e)                      -0.197
        EX_zn2(e)                      -0.002
Outflows:
        EX_co2(e)                      21.515
        EX_fe3(e)                      10.675
        EX_h2o(e)                      48.250
        EX_myrsACP                      0.045
        EX_tdeACP                       0.053
        EX_palmACP                      0.033
        EX_hdeACP                       0.039
        EX_ddcaACP                      0.080
        EX_dcaACP                       0.107
        EX_ocACP                        0.212
        Biomass                         0.787

Elapsed time is 4.513664 seconds.

Iteration 2
-----------

Biomass flux:   0.787129
Synthetic flux: [0.569028, 0.569028] of 5.098657
Knockout cost:  1
Knockouts:
        ((b0221))
Inflows:
        EX_ca2(e)                      -0.004
        EX_cl(e)                       -0.004
        EX_cobalt2(e)                  -0.002
        EX_cu2(e)                      -0.002
        EX_fe2(e)                     -10.687
        EX_glc(e)                     -10.000
        EX_h(e)                        -3.451
        EX_k(e)                        -0.140
        EX_mg2(e)                      -0.006
        EX_mn2(e)                      -0.002
```

FIG. 1A-continued

```
            EX_mobd(e)                  -0.002
            EX_nh4(e)                   -8.488
            EX_o2(e)                   -20.000
            EX_pi(e)                    -0.757
            EX_so4(e)                   -0.197
            EX_zn2(e)                   -0.002
Outflows:
            EX_co2(e)                   21.515
            EX_fe3(e)                   10.675
            EX_h2o(e)                   48.250
            EX_myrsACP                   0.045
            EX_tdeACP                    0.053
            EX_palmACP                   0.033
            EX_hdeACP                    0.039
            EX_ddcaACP                   0.080
            EX_dcaACP                    0.107
            EX_ocACP                     0.212
            Biomass                      0.787

Elapsed time is 8.260625 seconds.
Workspace saved to 'gdls.iaf1260-ffa.20100325T223942.methionine.mat'.
```

FIG. 1A-continued

```
modelname  = iaf1260-ffa
nbhdsz     = 2
M          = 1
maxknock   = 10
bruteforce = 0

Loading model "iaf1260-ffa" ...

nmetab = 583; nrxn = 1164; nbin = 663
Biomass flux:    0.890753
Synthetic flux:  [0.135156, 0.135156] of 5.098657
Inflows:
      EX_ca2(e)                  -0.004
      EX_cl(e)                   -0.004
      EX_cobalt2(e)              -0.003
      EX_cu2(e)                  -0.003
      EX_fe2(e)                  -0.007
      EX_fe3(e)                  -0.006
      EX_glc(e)                 -10.000
      EX_k(e)                    -0.158
      EX_mg2(e)                  -0.007
      EX_mn2(e)                  -0.003
      EX_mobd(e)                 -0.003
      EX_nh4(e)                  -9.606
      EX_o2(e)                  -19.349
      EX_pi(e)                   -0.856
      EX_so4(e)                  -0.223
      EX_zn2(e)                  -0.003
Outflows:
      EX_co2(e)                  21.897
      EX_h(e)                     8.181
      EX_h2o(e)                  45.543
      EX_myrsACP                  0.014
      EX_tdeACP                   0.032
      EX_palmACP                  0.013
      EX_hdeACP                   0.015
      EX_ddcaACP                  0.008
      EX_dcaACP                   0.009
      EX_ocACP                    0.045
      Biomass                     0.891

Performing 2-OPT local search ...

Iteration 1
-----------

Biomass flux:    0.651035
Synthetic flux:  [, 0.233820] of 5.098657
Knockout cost:   4
Knockouts:
      ((((b3386)_OR_(b4301))))
      ((((b0008)_OR_(b2464))))
Inflows:
      EX_ca2(e)                  -0.003
      EX_cl(e)                   -0.003
      EX_cobalt2(e)              -0.002
      EX_cu2(e)                  -0.002
      EX_fe2(e)                 -16.915
      EX_glc(e)                 -10.000
      EX_h(e)                   -10.628
      EX_k(e)                    -0.116
      EX_mg2(e)                  -0.005
      EX_mn2(e)                  -0.002
      EX_mobd(e)                 -0.002
      EX_nh4(e)                  -7.142
```

FIG. 1B

```
        EX_o2(e)                        -20.000
        EX_pi(e)                         -0.868
        EX_so4(e)                        -0.163
        EX_zn2(e)                        -0.002
Outflows:
        EX_co2(e)                        20.121
        EX_colipa(e)                      0.061
        EX_fe3(e)                        16.905
        EX_h2o(e)                        47.696
        EX_myrsACP                        0.017
        EX_tdeACP                         0.031
        EX_palmACP                        0.009
        EX_hdeACP                         0.011
        EX_ddcaACP                        0.039
        EX_dcaACP                         0.044
        EX_ocACP                          0.083
        Biomass                           0.651

Elapsed time is 52.047621 seconds.

Iteration 2
-----------

Biomass flux:    0.649154
Synthetic flux:  [0.256376, 0.256376] of 5.098657
Knockout cost:   7
Knockouts:
        ((((b1701)_OR_(b1805))))
        ((b4015))
        ((((b3386)_OR_(b4301))))
        ((((b0008)_OR_(b2464))))
Inflows:
        EX_ca2(e)                        -0.003
        EX_cl(e)                         -0.003
        EX_cobalt2(e)                    -0.002
        EX_cu2(e)                        -0.002
        EX_fe2(e)                       -17.489
        EX_glc(e)                       -10.000
        EX_h(e)                         -11.220
        EX_k(e)                          -0.115
        EX_mg2(e)                        -0.005
        EX_mn2(e)                        -0.002
        EX_mobd(e)                       -0.002
        EX_nh4(e)                        -7.121
        EX_o2(e)                        -20.000
        EX_pi(e)                         -0.866
        EX_so4(e)                        -0.162
        EX_zn2(e)                        -0.002
Outflows:
        EX_co2(e)                        20.046
        EX_colipa(e)                      0.060
        EX_fe3(e)                        17.479
        EX_h2o(e)                        47.857
        EX_myrsACP                        0.017
        EX_tdeACP                         0.012
        EX_palmACP                        0.009
        EX_hdeACP                         0.011
        EX_ddcaACP                        0.058
        EX_dcaACP                         0.064
        EX_ocACP                          0.085
        Biomass                           0.649

Elapsed time is 88.707067 seconds.
```

FIG. 1B-continued

```
Iteration 3
-----------

Biomass flux:    0.649154
Synthetic flux:  [0.256376, 0.256376] of 5.098657
Knockout cost:   7
Knockouts:
     ((((b1701)_OR_(b1805))))
     ((b4015))
     ((((b3386)_OR_(b4301))))
     ((((b0008)_OR_(b2464))))
Inflows:
     EX_ca2(e)              -0.003
     EX_cl(e)               -0.003
     EX_cobalt2(e)          -0.002
     EX_cu2(e)              -0.002
     EX_fe2(e)             -17.489
     EX_glc(e)             -10.000
     EX_h(e)               -11.220
     EX_k(e)                -0.115
     EX_mg2(e)              -0.005
     EX_mn2(e)              -0.002
     EX_mobd(e)             -0.002
     EX_nh4(e)              -7.121
     EX_o2(e)              -20.000
     EX_pi(e)               -0.866
     EX_so4(e)              -0.162
     EX_zn2(e)              -0.002
Outflows:
     EX_co2(e)              20.046
     EX_colipa(e)            0.060
     EX_fe3(e)              17.479
     EX_h2o(e)              47.857
     EX_myrsACP              0.017
     EX_tdeACP               0.012
     EX_palmACP              0.009
     EX_hdeACP               0.011
     EX_ddcaACP              0.058
     EX_dcaACP               0.064
     EX_ocACP                0.085
     Biomass                 0.649

Elapsed time is 115.618247 seconds.
Workspace saved to 'gdls.iaf1260-ffa.20100325T224500.methionine.mat'.
```

FIG. 1B-continued

GENETICALLY ENGINEERED MICROBES AND USES THEREOF

CROSS REFERENCE TO RELATED APPLICATION

This application is the U.S. National Phase of International Patent Application Serial No. PCT/US12/27219, filed Mar. 1, 2012, which claims priority of U.S. Provisional Application No. 61/447,746 filed on Mar. 1, 2011. The content of the foregoing applications are incorporated herein by reference in their entireties.

FIELD OF INVENTION

This invention relates to genetically engineered microbes that can be used to produce fatty acids at a high level for making fuels and related methods.

BACKGROUND OF INVENTION

The industrialized world has been relying on fossil fuels for centuries to provide, among others, electricity, gasoline, jet fuel, plastics, and so on. As supplies of fossil fuels are limited, there is a critical need to develop alternative energy sources, including renewable energy. Microbes offer great promise to contribute a significant portion of the renewable energy.

Genome-scale flux-balance analysis (FBA) modeling has been shown to be useful for the in silico design of engineered strains of microbes that overproduce diverse targets. These engineered strains include *Escherichia coli* that overproduce lycopene (Alper et al. 2005 Metabolic Engineering 7(3): 155-164; and Alper et al. 2005 Nature Biotechnology 23(5): 612-616), lactic acid (Fong et al. 2005 Biotechnology and Bioengineering 91(5): 643-648), succinic acid (Lee et al. 2005 Applied and Environmental Microbiology 71(12): 7880-7887; and Wang et al. 2006 Applied Microbiology and Biotechnology 73(4): 887-894), L-valine (Park et al. 2007 Proceedings of the National Academy of Sciences, USA 104(19): 797-7802), and L-threonine (Lee et al. 2007 Molecular Systems Biology 3: 149) and strains of *Saccharomyces cerevisiae* that overproduce ethanol (Bro et al. 2006 Metabolic Engineering 8(2): 102-111; and Hjersted et al. 2007 Biotechnology and Bioengineering 97(5): 1190-1204). FBA models allow the result of various genetic manipulations strategies to be predicted. As a result, the space of possible genetic manipulations can be computationally searched for the strategy that results in the desired metabolic network state. This space is vast, and algorithms must be designed to search the space efficiently.

Transforming bi-level optimization of FBA models to single level mixed-integer linear programming (MILP) problems (Burgard et al. 2003 Biotechnology and Bioengineering 84(6): 647-657; Pharkya et al. 2004 Genome Research 14(11): 2367-2376; and Pharkya et al. 2006 Metabolic Engineering 8(1): 1-13) has resulted in computational methods that efficiently search the space of genetic manipulations. This approach is much more efficient than exhaustive, brute-force search, but it is nevertheless very computationally intensive. The runtimes scale exponentially as the number of manipulations allowed in the final design increases. For large models, such as the latest genome-scale model of *E. coli* K-12 MG1655 (Feist et al. 2007 Molecular Systems Biology 3: 121), iAF1260, it was found that this runtime generally proves prohibitive for designs involving more than a few manipulations. Given the fact that useful metabolically engineered strains often require many genetic manipulations (such as the artemisinic-acid-producing strain of *S. cerevisiae* by Ro et al. 2006, Nature 440(7086): 940-943), which required the addition of three genes and the up- or down-regulation of four genes) and that the number of reactions, metabolites, and genes in metabolic, models continues to grow (Feist et al. 2008 Nature Biotechnology 26(6): 659-667). There is a need for more efficient computational search techniques for effective in silico design.

SUMMARY OF INVENTION

This invention is based, at least in part, on an unexpected discovery of a new methodology for identifying a target gene for a genetic alteration, where an engineered microbe having the genetic alteration produces a fatty acid at a level higher than a control microbe that lacks the genetic alteration.

Accordingly, one aspect of the invention features a method for constructing a model for identifying a target gene for a genetic alteration. The method includes step of obtaining a genome-scale flux-balance analysis (FBA) model; adding to the model a component that models a thioesterase shunt, wherein the added component forces a fraction of the flux passing through a fatty acyl-ACP compound in the model through the following reaction:

fatty acyl-ACP[c]→ACP[c]+free fatty acid[e], wherein [c] represents the cytoplasm compartment and [e] represents extracellular space; obtaining a biological optimal flux distribution; and displaying a record comprising a gene returned by the model, whereby the gene is the target for the genetic alteration. An engineered microbe having the genetic alteration produces a fatty acid at a level higher than a control microbe that is identical to the engineered microbe except that the control microbe lacks the genetic alteration.

In a second aspect, the invention features a method for identifying a target for a genetic alteration. An engineered microbe having the genetic alteration produces a fatty acid at a level higher than a control microbe that is identical to the engineered microbe except that the control microbe lacks the genetic alteration. The method includes obtaining one or more genes using the model constructed by the method described above.

In the above methods, the microbe can be a bacterium (e.g., *E. coli*) or a yeast (e.g., *Saccharomyces cerevisiae*). The model can be an iAF1260 model as describe in Alper et al. 2005 Metabolic Engineering 7(3): 155-164; and Alper et al. 2005 Nature Biotechnology 23(5): 612-616; Fong et al. 2005 Biotechnology and Bioengineering 91(5): 643-648; Lee et al. 2005 Applied and Environmental Microbiology 71(12): 7880-7887; Wang et al. 2006 Applied Microbiology and Biotechnology 73(4): 887-894; Park et al. 2007 Proceedings of the National Academy of Sciences, USA 104 (19): 797-7802; Lee et al. 2007 Molecular Systems Biology 3: 149; Bro et al. 2006 Metabolic Engineering 8(2): 102-111; and Hjersted et al. 2007 Biotechnology and Bioengineering 97(5): 1190-1204. These publications are incorporated in this application by reference in their entirety. In one embodiment, the biological optimal flux distribution is obtained by a Genetic Design through Local Search (GDLS) approach. The GDLS can be carried out in the manner described in Lun et al. 2009 Molecular Systems Biology 5: 296, the content of which is hereby incorporated by reference in its entirety. The genetic alteration can be an alteration of two or more genes. The genetic alteration can be a knockout of a gene or overexpression of a gene.

In a third aspect, the invention features a machine-readable medium for carrying out the methods described above. The machine-readable medium has machine-readable instructions encoded thereon which, when executed by a processor, cause a machine having or linked to the processor to execute each of the methods.

In a fourth aspect, the invention features a machine-readable medium on which is stored a database capable of configuring a computer to respond to queries based on a plurality of records or values belonging to the database. Each of the records has one or more of the following values:

a genotype value that identifies a genotype of a microbe having one or more genetic alterations;

a gene value that identifies a gene having a genetic alteration;

a fatty acid value that identifies a fatty acid;

a biomass flux value that identifies a biomass flux; and a free fatty acid flux value that identifies a free fatty acid flux.

The biomass flux and free fatty acid flux are obtained using the model of methods described above.

This invention also features a computer system having the above-mentioned machine-readable medium and a user interface capable of receiving the above-mentioned data and displaying the above-mentioned record.

In a fifth aspect, the invention features an isolated or cultured cell that lacks a functional gene, wherein the gene is selected from the group consisting of fadE (e.g., GenBank Accession NO.: NP_414756), rpe (e.g., GenBank Accession NO.: NP_417845), sgcE (e.g., GenBank Accession NO.: NP_418721), talA e.g., GenBank Accession NO.: (NP_416959), and talB (e.g., GenBank Accession NO.: NP_414549) genes and a homologue thereof. In one example, the cell lacks a functional fadE gene (i.e., fadE gene knockout); in another, the cell lacks both functional rpe/sgcE gene and talAB gene (i.e., a double-knockout of these two genes). The cell can be a bacterium cell (e.g., *E. coli*) or a yeast cell (e.g., *Saccharomyces cerevisiae*). Preferably, the cell is an *E. coli.* cell, such as a K-12 MG1665 cell. The cell can be one expressing a thioesterase, such as *E. coli* thioesterase gene tesA, 'tesA, or plant thioesterases as described in Cho et al. 1995 J. Biol. Chem. 270(9): 4216-4219, Voelker et al. 1994 J. Bacteriol. 176(23): 7320-7327; Dehesh et al. 1996 The Plant Journal 9(2): 167-172; and Steen et al. 2010 Nature 463(7280): 559-562). These publications are incorporated by reference in their entirety.

In a sixth aspect, the invention features a method of producing a fatty acid. The method includes steps of culturing the above-described cell in a culture under conditions allowing producing of the fatty acid by the cell, and obtaining the fatty acid from the culture.

In a seventh aspect, the invention features a method of a hydrocarbon product. Briefly, fatty acids can be converted to jet fuel and gasoline by thermally decarboxylating fatty acids to form linear hydrocarbons, then hydrocracking and isomerizing the fatty acids to form branched hydrocarbons in the jet fuel or gasoline range. The method can be conducted in the manner described in WO 2007027955 or US Application No. 20080229654. These publications are incorporated by reference in their entirety. For example, the method can include steps performing thermal decarboxylation on fatty acids to form a thermal decarboxylation product stream; hydrocracking the thermal decarboxylation product stream; and isolating a product in the gasoline, jet, or diesel fuel range. At least a portion of the fatty acids are derived from the cell described above. Also all or a portion of the product can be subjected to isomerization conditions, hydrogenation, hydrotreatment, and/or hydrofinishing conditions.

The details of one or more embodiments of the invention are set forth in the description below. Other features, objects, and advantages of the invention will be apparent from the description and from the claims.

DESCRIPTION OF DRAWING

FIGS. 1A and B show results of genetic design through local searches for genetic alteration strategies for fatty acid overproduction in *E. coli* K-12 MG1655 with thioesterase shunt.

DETAILED DESCRIPTION OF THE INVENTION

Figure 2:
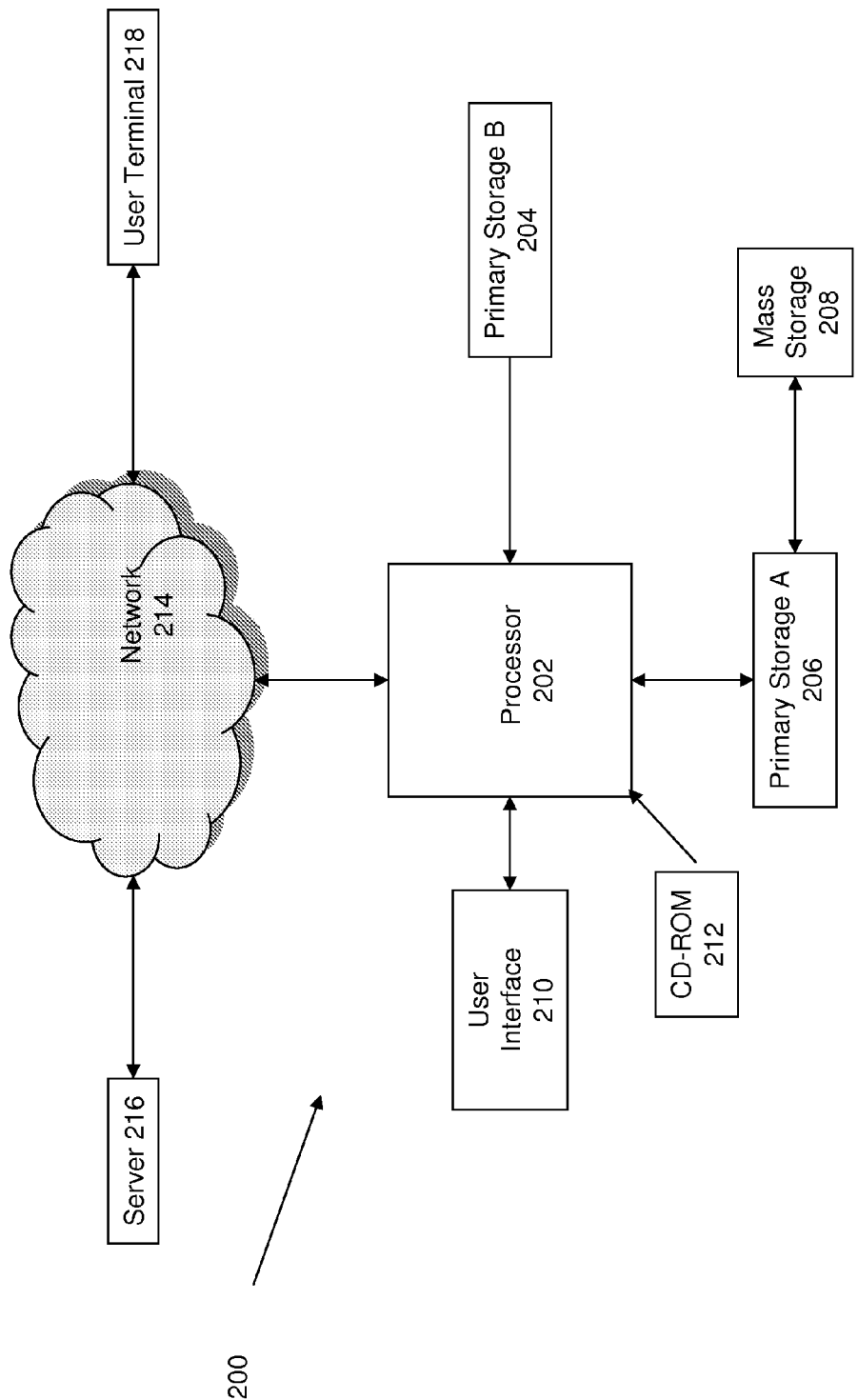
FIG. 2 is a diagram showing an exemplary computer system.

This invention provides to methods and systems for identifying candidates of genetic alterations that result in fatty acid overproduction in microbes, such as bacteria (e.g., *E. coli*). Fatty acids produced by these microbes can be used for producing biofuels. The economical and sustainable production of liquid transportation fuels that are not derived from fossil fuels, particularly crude oil, is a pressing problem concerning U.S. national interests and the world more broadly. Lipid biofuels, including biodiesel, biogasoline, and biojet fuel, can be produced chemically or biologically from fatty acids. This invention provides a novel computer modeling method that can be applied to any metabolic engineering problem requiring the insertion of genes under artificial transcriptional control. This invention also provides a specific application of this method to the problem of producing fatty acids using *Escherichia coli*. As an example, mutant strains of *E. coli* K-12 MG1655, which were developed as a result of this modeling method, have significantly increased fatty acid production over the wild type strain.

In one embodiment, this invention uses a two-stage process for producing jet fuel from food and non-food feed stocks. First, a genetically-engineered microorganism is used to convert the feedstock (e.g., various biomasses) into fatty acids. This organism is produced using a computational design process to identify favorable genetic modifications. Second, fatty acids are converted into jet fuel using a chemical process. The jet fuel can be domestically produced and can be used by the aviation and defense industries.

Methodology

In one aspect, this application provides a highly efficient analysis methodology for identifying candidates of genetic alterations that result in fatty acid overproduction in microbes. The methodology is based, at least in part, on an efficient computational method for in silico design—GDLS (Genetic Design through Local Search, Lun et al. 2009 Molecular Systems Biology 5: 296). GDLS is a scalable heuristic algorithmic method that employs an approach based on local search with multiple search paths which results in effective, low-complexity search of the space of genetic manipulations. Thus, GDLS is able to find genetic designs with greater in silico production of desired metabolites than can be feasibly found using globally-optimal search and performs favorably in comparison to heuristic searches based on evolutionary algorithms and simulated annealing.

As disclosed herein, GDLS can be applied to find genetic design strategies for overproducing hydrocarbon such as acetate and succinate using *E. coli*, which yielded results that were consistent with previous experimental studies. These compounds—acetate and succinate—are naturally produced and secreted by *E. coli*, and the design strategies described herein improve the efficiency of converting the feedstock, glucose, into the desired compound by linking the organism's biomass production with its production of the desired compound.

There are also many metabolites of interest that are not naturally produced and secreted by *E. coli* or other industrially attractive microbe. In these cases, exogenous genes must be introduced to cause the desired compound to be produced and secreted. This is the case with fatty acid production using *E. coli*. *E. coli* cells naturally produce fatty acids to make phospholipids that are incorporated into cellular components, but the fatty acids are not naturally secreted into the growth medium. Because there is no natural metabolic sink for fatty acids, it is difficult to substantially increase their production. By introducing either a modified version of the *E. coli* thioesterase gene teas (Cho et al. 1995 J. Biol. Chem. 270(9): 4216-4219) 'tesA, or certain plant thioesterases (Voelker et al. 1994 J. Bacteriol. 176(23): 7320-7327; Dehesh et al. 1996 The Plant Journal 9(2): 167-172; and Steen et al. 2010 Nature 463(7280): 559-562) into *E. coli*, however, the organism will secrete free fatty acids, and the production of fatty acids becomes decoupled from synthesis of cellular components, allowing for overproduction.

The likely mechanism of these thioesterases is that they disrupt the natural fatty acid biosynthesis pathway, where fatty acids are bound to ACPs (acyl carrier proteins) and form fatty acyl-ACPs. The thioesterases cleave the fatty acids from the ACPs during this elongation process, leaving free fatty acids that then diffuse out of the cell into the surrounding media Cho et al. 1995 J. Biol. Chem. 270(9): 4216-4219.

These thioesterases are genetically introduced using artificial promoters that are induced or constitutively expressed. Therefore, they are not under the natural regulatory control of the organism, and they form an artificial metabolic "shunt". This poses a problem for FBA, which assumes that, under certain constraints imposed on the capabilities of the organism, most importantly the stoichiometric constraints imposed by the enzymes it is capable of producing, the organism regulates expression so as to achieve its biological objective, which is typically assumed to be the maximization of biomass production.

The present invention provides a method for modeling such artificial shunts by extending FBA. By coupling this method with computational genetic design methods such as GDLS, one can obtain genetic design strategies for organisms containing such shunts. As shown in the example below, this approach was applied to the problem of overproducing fatty acids using *E. coli* with a thioesterase under artificial regulatory control, and it was shown that genetic designs obtained using the methodology of this invention resulted in overproduction of free fatty acids.

As shown in the example below, the methodology successfully identified genetic alterations that can be used to increase fatty acid production. The methodology allows microbes, such as *E. coli* and other bacteria, to be engineered for high-efficiency production of fatty acids. While bacteria can already be engineered to produce fatty acids, the greater the efficiency of the process in terms of its ability to produce high yields of fatty acids for a given amount of feedstock, the cheaper the process.

Computer Products, Systems, and Instruments

The computational methodology of this invention can be incorporated into a multiplicity of suitable computer products, systems, and/or information instruments. User interface methods known in the information processing art can be used in the systems of this invention.

1. Computer Software

For example, the above-disclosed methodology or components thereof can be embodied in a fixed medium (e.g., a computer accessible/computer readable medium program component containing logic instructions or data, or both), that when loaded into an appropriately configured computing device can cause that device to perform operations to the invention. In various embodiments a fixed medium component containing logic instructions can be delivered to a viewer on a fixed medium for physically loading into a viewer's computer or a fixed medium containing logic instructions can reside on a remote server that a viewer can access through a communication medium in order to download a program component.

Examples of a tangible computer-readable medium suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

2. Database

The above-described data and information generated using the methodology of this invention can be used to establish a database, i.e., a collection of data, which can be used to analyze and respond to queries. In one embodiment, the database includes one or more records for organizing the raw data sets and information sets in a particular hierarchy or directory (e.g., a hierarchy of studies and projects). In addition, the database may include information correlating the records to one another, a list of globally unique terms or identifiers for cell lines, genes, chemical or metabolism reactions, or other features. Such a database also contains a taxonomy that contains a list of all tags (keywords) for different genotypes, phenotypes, cells, as well as their relationships.

In one embodiment, the database contains data from a number of sources, including data from external sources, such as public databases). In addition, the database can include proprietary data obtained and processed by the database developer or user. A database may be updated by a developer or user as new public or private information from biological or chemical experiments becomes available. Once imported, all data are correlated with other information in the database so as to enable users to interrogate cell lines, genes, chemical or metabolism reactions, genotypes, phenotypes, as well as their relationships across the entire information space.

3. Computer Hardware

In another aspect, the invention provides an apparatus for performing the above-mentioned operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps.

FIG. 2 illustrates an exemplary computer system (200) that, when appropriately configured or designed, can serve as a computational apparatus according to certain embodiments. The computer system 200 includes any number of processors 202 (i.e., central processing units, or CPUs) that are coupled to storage devices including primary storage 206 (typically a random access memory, or RAM), primary storage 204 (typically a read only memory, or ROM). CPU 202 may be of various types including microcontrollers and microprocessors such as programmable devices (e.g., CPLDs and FPGAs) and non-programmable devices such as gate array ASICs or general-purpose microprocessors. In the depicted embodiment, primary storage 204 acts to transfer data and instructions uni-directionally to the CPU and primary storage 206 is used typically to transfer data and instructions in a bi-directional manner. Both of these primary storage devices may include any suitable computer-readable media such as those described above. A mass storage device 208 is also coupled bi-directionally to primary storage 206 and provides additional data storage capacity and may include any of the computer-readable media described above. Mass storage device 208 may be used to store programs, data and the like and is typically a secondary storage medium such as a hard disk. Frequently, such programs, data and the like are temporarily copied to primary memory 206 for execution on CPU 202. The information retained within the mass storage device 208, may, in appropriate cases, be incorporated in standard fashion as part of primary storage 204. A specific mass storage device such as a CD-ROM 612 may also pass data uni-directionally to the CPU or primary storage.

CPU 202 is also coupled to an interface 610 that connects to one or more input/output devices such as video monitors, track balls, mice, keyboards, microphones, touch-sensitive displays, transducer card readers, magnetic or paper tape readers, tablets, styluses, voice or handwriting recognition peripherals, USB ports, or other well-known input devices such as other computers. Finally, CPU 202 optionally may be coupled to an external device such as a database or a computer or telecommunications network using an external connection as shown generally at network 614. With such a connection, it is contemplated that the CPU might receive information from the network, or might output information to the network in the course of performing the method steps described herein.

In one embodiment, a system such as computer system 200 is used as a special purpose data import, data correlation, and querying system capable of performing some or all of the tasks described herein. System 200 may also serve as various other tools associated with database described above and querying such as a data capture tool. Information and programs, including data files can be provided via a network connection 214 for access or downloading from server system 216. Alternatively, such information, programs and files can be provided to the researcher on a storage device. In a specific embodiment, the computer system 200 is directly coupled to a data acquisition system such as a high-throughput screening system that captures data from samples. Data from such systems are provided via interface 210 for analysis by system 200. Alternatively, the data processed by system 200 are provided from a data storage source such as a database or other repository of relevant data. Once in apparatus 200, a memory device such as primary storage 206 or mass storage 208 buffers or stores, at least temporarily, relevant data. The memory may also store various routines and/or programs for importing, analyzing and presenting the data, including importing the above-described data sets, correlating data sets with one another and with feature groups, generating and running queries, etc.

In certain embodiments, the system of this invention may include one or more user terminals (218). User terminals can include any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms. A server (216) in communication with a user terminal may include a server device or decentralized server devices, and may include mainframe computers, mini computers, super computers, personal computers, or combinations thereof. A plurality of server systems may also be used without departing from the scope of the present invention. User terminals and a server system may communicate with each other through the network 214. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Genetically Engineered Cells and Production of Fatty Acid

The above-described computational methodology successfully identified genetic alterations that can be used to increase fatty acid production. Accordingly, microbes, such as *E. coli* and other bacteria, can be engineered to have those alterations and are useful for high-efficiency production of fatty acids.

In one aspect, the invention provides a method of producing a fatty acid. The method includes culturing the above-mentioned genetically engineered host cell in the presence of a carbon source. In one example, the host cell is genetically engineered to lack one or more of a number of functional genes or to have a reduced expression levels of the one or more genes as compared to wildtype cells. Examples of these genes include fadE, rpe, sgcE, talA and talB. The host cell can also be engineered to over-express a gene encoding a thioesterase, such as tesA, 'tesA, tesB, fatB, fatB2, fatB3, fatA1. In some embodiments, the method further comprises isolating the fatty acid.

In some embodiments, the fatty acid is present in the extracellular environment. In that case, the fatty acid can be isolated from the extracellular environment of the host cell using techniques known in the art. In some embodiments, the fatty acid is spontaneously secreted, partially or completely, from the host cell. In alternative embodiments, the fatty acid is transported into the extracellular environment, optionally with the aid of one or more suitable transport proteins. In other embodiments, the fatty acid is passively transported into the extracellular environment.

In some embodiments, the host cell is cultured in a culture medium containing an initial concentration of the carbon source of about 0.2% to 10% (w/v) or 2 g/L to about 100 g/L (e.g., about 2 to 10, 10 to 20, 20 to 30, 30 to 40, 40 to 50 g/L) of a carbon source. In exemplary embodiments, the culture medium contains an initial concentration of about 2 g/L or more of a carbon source. To that end, the method can further include a step of monitoring the level of the carbon source in the culture medium. In some embodiments, the method further includes adding a supplemental carbon source to the culture medium when the level of the carbon source in the medium is less than about 0.5 g/L (e.g., 0.4, 0.3, 0.2, or 0.1 g/L).

The methods disclosed herein can be performed using glucose as a carbon source. In that case, microorganisms can be grown in a culture medium containing an initial glucose concentration of about 2 g/L to about 50 g/L, such as 20 g/L (i.e., 2% w/v). Since the glucose concentration of the medium decreases from the initial concentration as the microorganisms consume the glucose, a concentration of about 0 g/L to about 5 g/L glucose is maintained in the culture medium during the fatty ester production process. Glucose can be fed to the microorganisms in a solution of about 50% to about 65% glucose. In some instances, the feed rate of glucose is set to match the cells' growth rate to avoid excess accumulation of glucose. In certain embodiment, fatty acids can be produced from carbohydrates other than glucose, including but not limited to fructose, hydrolyzed sucrose, hydrolyzed molasses and glycerol.

Various cells can be used as the host cell in the above-described method. Examples include a mammalian cell, plant cell, insect cell, yeast cell, fungus cell, filamentous fungi cell, and bacterial cell. In one example, the host cell is selected from the genus *Escherichia*, *Bacillus*, *Lactobacillus*, *Rhodococcus*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophtora*, *Penicillium*, *Phanerochaete*, *Pleurotus*, *Trametes*, *Chrysosporium*, *Saccharomyces*, *Stenotrophamonas*, *Schizosaccharomyces*, *Yarrowia*, or *Streptomyces*. In a preferred embodiment, the host cell is an *E. coli* cell. Various methods well known in the art can be used to genetically engineer host cells to knockout one or more genes or to over-express one or more of other genes.

As used herein, the term "deletion" or "knockout" means modifying or inactivating a polynucleotide sequence that encodes a target protein in order to reduce or eliminate the function of the target protein. A polynucleotide deletion can be performed by methods well known in the art (See, e.g., Datsenko et al., Proc. Nat. Acad. Sci. USA, 97:6640-45, 2000 or International Patent Application Nos. PCT/US2007/011923 and PCT/US2008/058788). "Gene knockout," as used herein, refers to a procedure by which a gene encoding a target protein is modified or inactivated so to reduce or eliminate the function of the intact protein. Inactivation of the gene may be performed by general methods such as mutagenesis by UV irradiation or treatment with N-methyl-N'-nitro-N-nitrosoguanidine, site-directed mutagenesis, homologous recombination, insertion-deletion mutagenesis, or "Red-driven integration" (Datsenko et al., Proc. Natl. Acad. Sci. USA, 97:6640-45, 2000).

For example, in one embodiment, a construct is introduced into a host cell, such that it is possible to select for homologous recombination events in the host cell. One of skill in the art can readily design a knock-out construct including both positive and negative selection genes for efficiently selecting transfected cells that undergo a homologous recombination event with the construct. The alteration in the host cell may be obtained, for example, by replacing through a single or double crossover recombination a wild type DNA sequence by a DNA sequence containing the alteration. For convenient selection of transformants, the alteration may, for example, be a DNA sequence encoding an antibiotic resistance marker or a gene complementing a possible auxotrophy of the host cell. Mutations include, but are not limited to, deletion-insertion mutations. An example of such an alteration includes a gene disruption, i.e., a perturbation of a gene such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some instances, the entire mRNA for the gene is absent. In other situations, the amount of mRNA produced varies.

As used herein, "overexpress" means to express or cause to be expressed or produced a nucleic acid, polypeptide, or hydrocarbon in a cell at a greater concentration than is normally expressed in a corresponding wild-type cell. For example, a polypeptide can be "overexpressed" in a recombinant host cell when the polypeptide is present in a greater concentration in the recombinant host cell compared to its concentration in a non-recombinant host cell of the same species.

For overexpression a polypeptide, the methods can include the use of vectors, preferably expression vectors, containing a nucleic acid encoding a desired polypeptide, such as a thioesterase, as described herein, polypeptide variant, or a fragment thereof. Those skilled in the art will appreciate a variety of viral vectors (for example, retroviral vectors, lentiviral vectors, adenoviral vectors, and adeno-associated viral vectors) and non-viral vectors can be used in the methods described herein.

Expression of polypeptides in prokaryotes, for example, *E. coli*, can often be carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (1) to increase expression of the recombinant polypeptide; (2) to increase the solubility of the recombinant polypeptide; and (3) to aid in the purification of the recombinant polypeptide by acting as a ligand in affinity purification.

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. Sambrook et al., Molecular Cloning: A Laboratory Manual. 2nd, ed., Cold Spring Harbor Laboratory, Cold Spring Harbor Laboratory Press, Cold Spring Harbor, N.Y. (1989).

For stable transformation of bacterial cells, only a small fraction of cells will take-up and replicate the expression vector depending upon the expression vector and transformation technique used. In order to identify and select these transformants, a gene that encodes a selectable marker (e.g., resistance to antibiotics) can be introduced into the host cells along with the gene of interest. Selectable markers include those that confer resistance to drugs, such as ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transfected with the introduced nucleic acid can be identified by drug selection (e.g., cells that have incorporated the selectable marker gene will survive, while the other cells die).

With the above-described host cells and methods, one can produce various fatty acids at concentrations shown in Table 2 below. The fatty acid produced during fermentation can be separated from the fermentation media. Any known technique for separating fatty acids from aqueous media can be used. For example, one can used a two phase (bi-phasic) separation process. This process involves fermenting the genetically engineered host cells under conditions sufficient to produce a fatty acid, allowing the fatty acid to collect in an organic phase, and separating the organic phase from the aqueous fermentation broth. This method can be practiced in both a batch and continuous fermentation processes.

Once fatty acids are collected, they can be converted to jet fuel and gasoline by thermally decarboxylating fatty acids to form linear hydrocarbons, then hydrocracking and isomerizing the fatty acids to form branched hydrocarbons in the jet fuel or gasoline range. The method can be conducted in the manner described in WO 2007027955 or US Application No. 20080229654. These publications are incorporated by reference in their entirety. For example, the method can include steps performing thermal decarboxylation on fatty acids to form a thermal decarboxylation product stream; hydrocracking the thermal decarboxylation product stream, and isolating a product in the gasoline, jet, or diesel fuel range. At least a portion of the fatty acids are derived from the cell described above. Also all or a portion of the product can be subjected to isomerization conditions, hydrogenation, hydrotreatment, and/or hydrofinishing conditions.

As used herein, the term "biodiesel" means a biofuel that can be a substitute of diesel, which is derived from petroleum. Biodiesel can be used in internal combustion diesel engines in either a pure form, which is referred to as neat biodiesel, or as a mixture in any concentration with petroleum-based diesel. In one embodiment, biodiesel can include esters or hydrocarbons, such as aldehydes, alkanes, or alkenes.

As used herein, the term "biofuel" refers to any fuel derived from biomass, biomass derivatives, or other biological sources. Biofuels can be substituted for petroleum based fuels. For example, biofuels are inclusive of transportation fuels (e.g., gasoline, diesel, jet fuel, etc.), heating fuels, and electricity-generating fuels. Biofuels are a renewable energy source.

As used herein, the term "biomass" refers to a carbon source derived from biological material. Biomass can be converted into a biofuel. One exemplary source of biomass is plant matter. For example, corn, sugar cane, or switchgrass can be used as biomass. Another non-limiting example of biomass is animal matter, for example cow manure. Biomass also includes waste products from industry, agriculture, forestry, and households. Examples of such waste products that can be used as biomass are fermentation waste, straw, lumber, sewage, garbage, and food leftovers. Biomass also includes sources of carbon, such as carbohydrates (e.g., monosaccharides, disaccharides, or polysaccharides).

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as methanol, ethanol, propanol, or mixtures thereof. The carbon source can also be a product of photosynthesis, including, but not limited to, glucose. A preferred carbon source is biomass. Another preferred carbon source is glucose.

As used herein, the term "conditions sufficient to allow expression" means any conditions that allow a host cell to produce a desired product, such as a polypeptide, fatty acid, or its derives described herein. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source, such as glucose, fructose, cellulose, or the like, that can be metabolized by a host cell directly. In addition, enzymes can be used in the medium to facilitate the mobilization (e.g., the depolymerization of starch or cellulose to fermentable sugars) and subsequent metabolism of the carbon source.

As used herein, "conditions that permit product production" refers to any fermentation conditions that allow a production host to produce a desired product, such as fatty acid or fatty acid derivatives (e.g., fatty acids, hydrocarbons, fatty alcohols, waxes, or fatty esters). Fermentation conditions usually comprise many parameters. Exemplary conditions include, but are not limited to, temperature ranges, levels of aeration, and media composition. Each of these conditions, individually and/or in combination, allows the production host to grow.

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used.

As used herein, the term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway.

As used herein, the term "fatty acid biosynthetic pathway" means a biosynthetic pathway that produces fatty acids. The fatty acid biosynthetic pathway includes fatty acid enzymes that can be engineered, as described herein, to produce fatty acids, and in some embodiments can be expressed with additional enzymes to produce fatty acids having desired carbon chain characteristics.

As used herein, the term "fatty acid derivative" means products made in part from the fatty acid biosynthetic pathway of the production host organism. Fatty acid derivative also includes products made in part from acyl-ACP or acyl-ACP derivatives. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, fatty acids, acyl-CoAs, fatty aldehydes, short and long chain alcohols, hydrocarbons, fatty alcohols, ketones, and esters (e.g., waxes, fatty acid esters, or fatty esters).

As used herein, a "vector" refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes various control elements, promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like.

As used herein "operably linked" or "operatively linked" means that a selected nucleotide sequence (e.g., encoding a polypeptide described herein) is in proximity with a promoter to allow the promoter to regulate expression of the selected nucleotide sequence. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

As used herein, "control element" means a transcriptional control element. Control elements include promoters and enhancers. The term "promoter" or "promoter sequence" refers to a DNA sequence that functions as a switch that activates the expression of a gene. If the gene is activated, it is said to be transcribed or participating in transcription. Transcription involves the synthesis of mRNA from the gene. A promoter, therefore, serves as a transcriptional regulatory element and also provides a site for initiation of transcription of the gene into mRNA. Control elements interact specifically with cellular proteins involved in transcription (Maniatis et al., Science 236:1237, 1987).

A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones, e.g., as these occur in a DNA library such as a cDNA or genomic DNA library. The nucleic acid described above can be used to express a protein of this invention. For this purpose, one can operatively link the nucleic acid to suitable regulatory sequences to generate an expression vector.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation). The peptide, polypeptide, or protein "of this invention" include recombinantly or synthetically produced fusion versions having the particular domains or portions that are soluble. The term also encompasses polypeptides that have an added amino-terminal methionine (useful for expression in prokaryotic cells).

A "recombinant" peptide, polypeptide, or protein refers to a peptide, polypeptide, or protein produced by recombinant DNA techniques; i.e., produced from cells transformed by an exogenous DNA construct encoding the desired peptide. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

As used herein, the term "substantially identical" (or "substantially homologous") is used to refer to a first amino acid or nucleotide sequence that contains a sufficient number of identical or equivalent (e.g., with a similar side chain) amino acid residues (e.g., conserved amino acid substitutions) or nucleotides to a second amino acid or nucleotide sequence such that the first and second amino acid or nucleotide sequences have similar activities.

EXAMPLE

Genome-Scale FBA Modeling

The genome-scale model of *E. coli*, iAF1260 was used in this example. This model consisted of three parts. From m metabolites and n reactions, an m×n stoichiometric matrix S was formed, whose ijth element $S_{ij}$ is the stoichiometric coefficient of metabolite i in reaction j. The vector of flux values of v, whose jth element $v_j$ is the flux though reaction j, were constrained by a lower bound vector a, whose jth element $a_j$ is the lower bound of the flux through reaction j, an upper bound vector b, whose jth element $b_j$ was the upper bound of the flux through reaction j. Finally, the linear objective is formed by multiplying the fluxes by an objective vector f, whose jth element $f_j$ is the weight of reaction j in the biological objective. Thus, a biologically-optimal flux distribution is obtained by solving $$\max f'v$$

subject to $Sv=0$, $$a \le v \le b. \quad (1)$$

Modeling of Metabolic Shunts

This example was limited to shunts of single reactants, i.e. each reaction that the shunt catalyzes involves only a single reactant. However, the same principles could be applied to cases involving two or more reactants in the shunt, though the modeling became substantially more complicated. For the thioesterase shunt, which catalyzes the reaction: fatty acyl-ACP$_{[c]} \rightarrow$ACP$_{[c]}$+free fatty acid$_{[e]}$, the single reactant case sufficed.

Without loss of generality, it was supposed that the shunt catalyzes a single reaction of the form $$A \rightarrow B.$$

In cases involving multiple reactions (as is the case for the thioesterase shunt, since there are multiple fatty acyl-ACP compounds in iAF1260), the transformation described below can be applied to each of the reactions in sequence. The number of products for the reaction is inconsequential.

Let the flux of this reaction be w, and suppose that there are K reactions, $v_1, v_2, \ldots, v_K$ in the model that involve A as a product and L reactions $v_{K+1}, v_{K+2}, \ldots, v_{K+L}$ that involve A as a reactant. The shunt was modeled by ensuring that some fraction $\alpha$ of the flux passing through A is forced through the shunt. Specifically, the following constraint was imposed $$w \ge \alpha \left\{ \sum_{k=1}^{K} \max(v_k, 0) + \sum_{k=K+1}^{L} \max(-v_k, 0) \right\}. \quad (2)$$

This constraint was enforced using the following linear constraints:

$$u_k = v_k + s_k, \; k=1, \ldots, K,$$

$$u_k = -v_k + s_k, \; k=K+1, \ldots, K+L,$$

$$w = \sum_{k=1}^{K+L} \alpha u_k,$$

$$u_k \ge 0, \; \forall k,$$

$$s_k \ge 0, \; \forall k, \quad (3)$$

which can be incorporated into the constraints of (1) to obtain a linear optimization problem that involves the shunt. In addition, the variables $u_k$ and $s_k$ can be associated with reactions and interpreted as fluxes, allowing the specific form of problem (1) to be used with a suitably defined stoichiometric matrix S. As a consequence, the approach used by GDLS (Lun et al. 2009 Molecular Systems Biology 5: 296) was applied to identify genetic design strategies with favorable values for the synthetic objective. The results were reported in Table 1 ($\alpha$:=0.2)

TABLE 1

Genetic design strategies for fatty acid overproduction in *E. coli* K-12 MG1655 with thioesterase shunt.

| Genotype | Number of knockouts | Biomass flux (h$^{-1}$) | Free fatty acid flux (mmol gDW$^{-1}$ h$^{-1}$) |
|---|---|---|---|
| WT 'tesA | 0 | 0.837675 | 0.336305 |
| ΔfadE 'tesA | 1 | 0.828200 | 0.397012 |
| Δrpe ΔsgcE ΔtalAB 'tesA | 2 | 0.592367 | 0.552849 |

In sum, the analysis was started with iAF1260 (Feist et al. 2007 Molecular Systems Biology 3: 121), the most recent and most detailed of the published FBA models of *E. coli* K-12 MG1655. Then, added to this model, was a component that modeled the thioesterase shunt (see above). Briefly, the added component forced a certain fraction of the flux passing through a fatty acyl-ACP compound in the model through the following reaction:

fatty acyl-ACP$_{[c]} \rightarrow$ACP$_{[c]}$+free fatty acid$_{[e]}$, where the chain length of the free fatty acid is appropriate for the specific fatty acyl-ACP involved in the reaction, and the subscripts indicate the cellular compartment of the compound, with c representing the cytoplasm, and e representing extracellular space.

Using GDLS, it was found that the optimal genetic design strategy involving one knockout was to knock out the fadE gene and that involving two knockouts was to knock out the isozymes rpe/sgcE and talAB (see Table 1). Of these strategies, one had already been previously experimentally implemented. Specifically, the fadE knockout coupled with the 'tesA thioesterase was shown to more than triple the yield of free fatty acids compared to wild-type *E. coli* DH1 with the 'tesA thioesterase, increasing the yield from 4% of the theoretical limit to 14% Steen et al. 2010 Nature 463(7280): 559-562.

An *E. coli* strain bearing the two knockout strategy involving rpe/sgcE and talAB was produced and tested for its fatty acid production. GDLS also produced other genetic strategies involving two or more knockouts.

In one example, strains of *E. coli* K-12 MG1655 bearing the fadE knockout and the rpe/sgcE and talAB knockouts were generated. The fatty acid yield from these strains on a two-day fermentation on 2% (w/v) glucose is summarized in Table 2. It was found that both the ΔfadE 'tesA and the Δrpe ΔsgcE ΔtalAB 'tesA strains show significantly increased fatty acid yield over wild type (7.1-fold and 3.9-fold respectively). The above-described modeling further predicts that the combination of all five knockouts (i.e. fadE, rpe, sgcE, talA and talB) has greater fatty acid yield than the two knockout strains tested so far.

TABLE 2

Yield of fatty acids of mutant strains of *E. coli* MG1655 K-12.

| | Yield (mg L$^{-1}$) | | | | | | | |
|---|---|---|---|---|---|---|---|---|
| | WT | | WT 'tesA | | ΔfadE 'tesA | | Δrpe ΔsgcE ΔtalAB 'tesA | |
| Fatty acid | Mean | Std. dev. | Mean | Std. dev. | Mean | Std. dev. | Mean | Std. dev. |
| C8:0 | 0.0 | 0.0 | 0.6 | 0.6 | 11.2 | 1.3 | 5.8 | 0.1 |
| C10:0 | 0.0 | 0.0 | 0.0 | 0.0 | 2.3 | 0.4 | 1.1 | 0.0 |

TABLE 2-continued

Yield of fatty acids of mutant strains of E. coli MG1655 K-12.

| | Yield (mg L$^{-1}$) | | | | | | | |
|---|---|---|---|---|---|---|---|---|
| | WT | | WT 'tesA | | ΔfadE 'tesA | | Δrpe ΔsgcE ΔtalAB 'tesA | |
| Fatty acid | Mean | Std. dev. | Mean | Std. dev. | Mean | Std. dev. | Mean | Std. dev. |
| C12:0 | 0.0 | 0.0 | 0.3 | 0.6 | 62.1 | 7.2 | 34.3 | 0.9 |
| C14:0 | 3.5 | 0.9 | 3.1 | 0.8 | 119.7 | 13.1 | 73.3 | 2.1 |
| C16:0 | 30.7 | 0.5 | 25.5 | 7.3 | 39.5 | 2.9 | 16.4 | 0.6 |
| C16:1 | 0.0 | 0.0 | 0.3 | 0.5 | 34.3 | 2.7 | 20.2 | 1.3 |
| C18:0 | 0.5 | 0.7 | 0.4 | 0.4 | 19.1 | 1.4 | 9.3 | 2.8 |
| C18:1 | 0.4 | 0.5 | 0.3 | 0.5 | 2.2 | 0.2 | 0.4 | 0.3 |
| C18:? | 4.5 | 2.5 | 1.7 | 0.1 | 0.2 | 0.3 | 0.0 | 0.0 |
| C18:2 | 0.0 | 0.0 | 0.0 | 0.0 | 0.3 | 0.6 | 0.0 | 0.0 |
| C20:0 | 1.3 | 1.8 | 1.6 | 1.4 | 0.8 | 1.3 | 0.0 | 0.0 |
| Total | 40.9 | 6.9 | 33.8 | 12.3 | 291.8 | 31.4 | 160.7 | 8.2 |

Note:
The mean and standard deviation are for three biological replicates of each strain, except WT, for which there were two replicates.

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. An isolated *E. coli* cell that lacks functional rpe, sgcE, talA, and talB genes.

2. The isolated cell of claim 1, wherein the cell lacks functional fadE gene.

3. The isolated cell of claim 1, wherein the cell is an *E. coli* K-12 MG1665 cell.

4. The isolated cell of claim 1, wherein the cell expresses a thioesterase.

5. A method of producing a fatty acid, comprising,
culturing the cell of claim 1 in a culture under conditions allowing producing of the fatty acid by the cell, and
obtaining the fatty acid from the culture.

6. A method of forming a hydrocarbon product, comprising
culturing the cell of claim 1 in a culture under conditions allowing production of fatty acids by the cell;
obtaining the fatty acids from the culture;
performing thermal decarboxylation on said fatty acids to form a thermal decarboxylation product stream;
hydrocracking the thermal decarboxylation product stream, and
isolating a product in the gasoline, jet, or diesel fuel range.

7. The method of claim 6, wherein the product is in the jet range.

8. The method of claim 6, wherein all or a portion of the product is subjected to isomerization conditions.

9. The method of claim 6, wherein all or a portion of the product is subjected to hydrogenation, hydrotreatment, and/or hydrofinishing conditions.

10. The isolated cell of claim 4, wherein the thioesterase is selected from the group consisting of tesA and leaderless thioesterase tesA ('tesA).

* * * * *

UNITED STATES PATENT AND TRADEMARK OFFICE
CERTIFICATE OF CORRECTION

PATENT NO. : 9,594,869 B2
APPLICATION NO. : 14/001299
DATED : March 14, 2017
INVENTOR(S) : Desmond S. Lun It is certified that error appears in the above-identified patent and that said Letters Patent is hereby corrected as shown below:

On the Title Page

In the Assignee: please add the following:
UNIVERSITY OF SOUTH AUSTRALIA, Adelaide SA (AU)

Signed and Sealed this
First Day of December, 2020

Andrei Iancu
*Director of the United States Patent and Trademark Office*